(12) United States Patent
Roulston et al.

(10) Patent No.: US 9,279,723 B2
(45) Date of Patent: Mar. 8, 2016

(54) TERAHERTZ SPECTROSCOPY SYSTEM AND METHOD

(75) Inventors: John F. Roulston, Edinburgh (GB); Daniel Mandelik, Rehovot (IL)

(73) Assignee: NOVATRANS GROUP SA, Vaumarcus (NE) (CH)

( * ) Notice: Subject to any disclaimer, the term of this patent is extended or adjusted under 35 U.S.C. 154(b) by 195 days.

(21) Appl. No.: 13/212,231

(22) Filed: Aug. 18, 2011

(65) Prior Publication Data
US 2012/0044479 A1 Feb. 23, 2012

Related U.S. Application Data

(60) Provisional application No. 61/375,203, filed on Aug. 19, 2010.

(51) Int. Cl.
| G01B 9/02 | (2006.01) |
| G01J 3/45 | (2006.01) |
| G01J 3/42 | (2006.01) |
| G01J 3/10 | (2006.01) |
| G01J 3/433 | (2006.01) |

(52) U.S. Cl.
CPC .. *G01J 3/42* (2013.01); *G01J 3/108* (2013.01); *G01J 3/4338* (2013.01)

(58) Field of Classification Search
USPC .......................................... 356/451, 456, 484
See application file for complete search history.

(56) References Cited

U.S. PATENT DOCUMENTS

| 6,348,683 | B1 | 2/2002 | Verghese | |
| 6,556,306 | B2 * | 4/2003 | Jiang et al. | 356/517 |
| 7,551,269 | B2 | 6/2009 | Itsuji | |
| 7,652,769 | B2 * | 1/2010 | Zhao et al. | 356/451 |
| 7,687,773 | B2 | 3/2010 | Siegel | |
| 7,986,413 | B2 * | 7/2011 | Federici | 356/456 |
| 8,300,229 | B2 * | 10/2012 | Cho et al. | 356/451 |
| 2013/0200263 | A1 * | 8/2013 | Logan et al. | 250/339.07 |

FOREIGN PATENT DOCUMENTS

| WO | 2007132459 A2 | 11/2007 |
| WO | 2011083462 A2 | 7/2011 |

OTHER PUBLICATIONS

Johnson, Jon L. et al. "Interferometric Imaging With Terahertz Pulses". IEEE Journal on Selected Topics in Quantum Electronics, vol. 7, No. 4, Jul./Aug. 2001, pp. 592-599.*
Pronin, A. V. et al. "Phase-sensitive terahertz spectroscopy with BOWs in reflection mode". 34th International Conference on Infrared, Millimeter, and Terahertz Waves (IRMMW-THz), Sep. 25, 2009, pp. 1-2.*

* cited by examiner

*Primary Examiner* — Michael A Lyons
(74) *Attorney, Agent, or Firm* — Browdy and Neimark, PLLC

(57) ABSTRACT

A terahertz spectrometer includes: a terahertz-wave emitter and a terahertz receiver elements. The terahertz wave generated by means of generating beat frequency corresponding to the difference between two rapidly tunable continuous wave lasers. Having a difference in time between the interrogating signal and the reference signal at the receiver end side, which corresponds to intermediate frequency (IF), not centered around the baseband, i.e. zero Hertz. The offset step size of the intermediate frequency from zero Hertz is linearly correlated to the position of the interrogated object position.

19 Claims, 10 Drawing Sheets

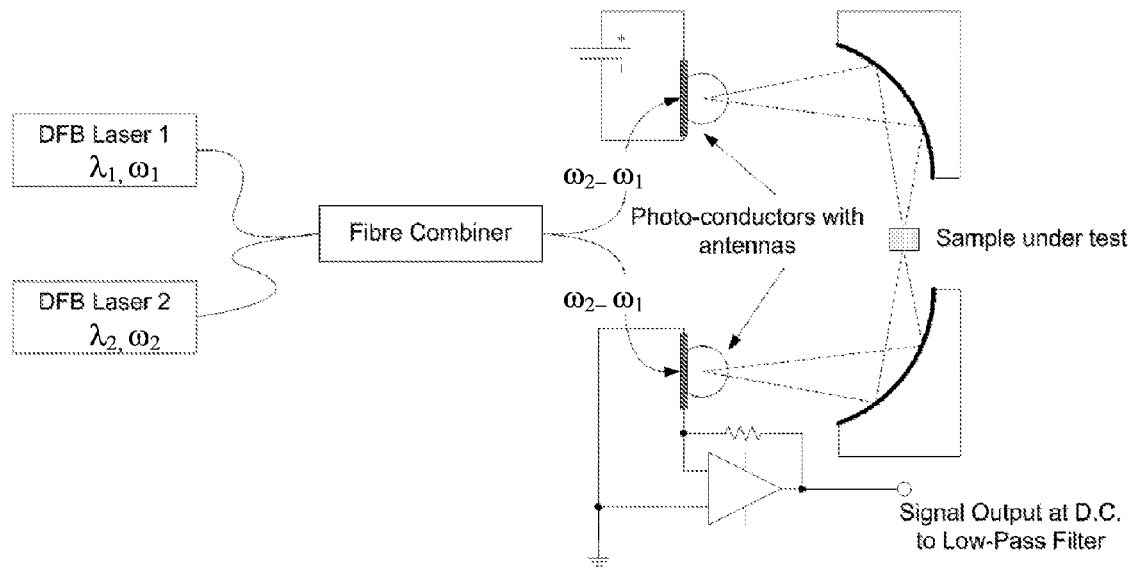
Fig. 1 (GENERAL ART)
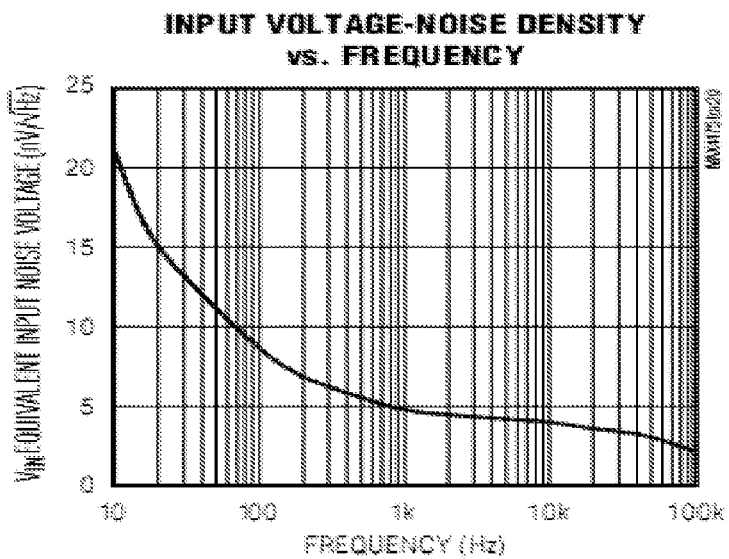
Fig. 2 (GENERAL ART)

TERAHERTZ SPECTROSCOPY SYSTEM AND METHOD

FIELD OF THE INVENTION

This invention relates to spectroscopic system and method and particularly to terahertz spectroscopy techniques.

BACKGROUND OF THE INVENTION

Spectroscopy is one of the main compelling applications of terahertz (THz) radiation. A typical THz Spectroscopy system includes a tunable THz transmitter capable of generating THz radiation for irradiating a sample and a THz detector capable of receiving THz radiation response from the irradiated sample and providing indication (electric signal) of the strength and propagation delay of the detected radiation from the sample. For example, the technique of obtaining information related to terahertz waves that are transmitted through or reflected by a sample is disclosed in U.S. Pat. No. 7,551,269.

A tunable THz transmission device typically includes two distributed feedback (DFB) lasers and a THz emitter associated with an antenna. One or both of the lasers are associated with a controllable thermo-electric-cooling (TEC) system which controls their operating temperatures and thus their output wavelengths. The lasers are used to illuminate the THz emitter (being typically a photo-conducting element) with a light signal containing an oscillating component at the beat frequency (difference frequency) of the lasers. In the emitter, a THz frequency current is excited while applying D.C. bias to the photo-conducting element which changes conductance at the beat frequency, causing the antenna coupled to it to radiate in the THz band. The frequency of the current in the antenna (and that of the emitted radiation) is the difference between the frequencies of the lasers (beat frequency), and thus tuning the frequency of the emitted THz radiation is achieved by changing the output frequency(ies) of one or both of the lasers. Such photo-mixing based THz emitter is described for example in WO 2007/132459, assigned to the assignee of the present application.

In a THz detection device (receiver), a responding THz radiation signal, (e.g. reflected, transmitted or scattered wave) from the irradiated sample is incident upon the antenna of the receiving device, which is constructed similarly to the emitting device. This THz signal induces a voltage across the receiving photo-conductor which, in this case, has substantially zero D.C. bias component. The conductivity of the receiving photo-conductor is also modulated at the optical beat frequency by the incident laser light in the same way as the transmitter device is modulated. If the beat frequency is constant, the THz modulation of the conductance interacting with the THz bias created by the signal from the antenna generates a low frequency (e.g. D.C.) signal component proportional to the amplitude of the incident THz wave and dependent on the relative phases of the received wave and the optical beat-frequency modulation. Such arrangement acts as a homodyne mixer in which the modulating optical beat frequency used in the emitter is also used as a reference signal (i.e. reference oscillator modulation) in the receiver. The intermediate frequency is centered around the D.C. (zero frequency), and the arrangement provides coherent detection. The desired signal centered at D.C. can be extracted by using a low pass filter.

The above is schematically shown in FIG. 1. Two light beams of wavelengths/frequencies ($\lambda_1$, $\omega_1$) and ($\lambda_2$, $\omega_2$) respectively are combined by a fiber splitter/combiner to propagate along a combined optical path, and then are split into two light components, each of a beat frequency ($\omega_2-\omega_1$) propagating along spatially separated optical paths towards respectively the transmitter- and receiver-antenna units. The light component at the receiver-antenna unit serves as a reference beam or local oscillator modulation. Each of the transmitter- and receiver-antenna units includes photo-conductors with antennas. Radiation emitted by the transmitter-antenna unit is directed (by a reflector) to the sample, and a radiation response of the sample (reflection from the sample) is directed (by another reflector) to the receiver-antenna unit. The latter includes a low-pass filter which operates to extract the desired signal. A photomixing based transceiver system of the kind described above is disclosed for example in U.S. Pat. No. 6,348,683.

A major disadvantage of such arrangement is associated with the fact that amplifiers exhibit high noise density at low frequencies called "flicker noise". Accordingly, in order to achieve reasonable signal to noise ratio, the signal (THs radiation incident onto the sample) has to be of as high as possible amplitude, and thus enabling the terahertz signal from the sample to be sufficiently strong when arriving at the receiver. Since the "flicker noise" and a detected signal (resulting from the interaction between the sample's response and reference signals) are in this case occupy frequency band with high density noise, a band pass filter (low pass filter) cannot be effectively utilized to filter out the noise. The severity of the flicker noise phenomenon is illustrated in FIG. 2 which shows noise density for a typical integrated-circuit amplifier (e.g. utilizing MAX4475 amplifier commercially available from Maxim. Integrated Products Inc). It may be seen that the noise density is rising rapidly as frequencies approach D.C. At 10 Hz the density is more than five times the density at 10 kHz, and at 1 Hz the density will be very much larger, probably several hundred time the density at 10 kHz.

Another technique of the kind specified is disclosed in U.S. Pat. No. 7,687,773. This technique relates to sub-millimeter wave frequency heterodyne imaging systems, more specifically, to a sub-millimeter wave frequency heterodyne detector system for imaging the magnitude and phase of transmitted power through or reflected power off of mechanically scanned samples at sub-millimeter wave frequencies.

GENERAL DESCRIPTION OF THE INVENTION

There is a need in the art in optimizing high-frequency spectroscopy (THz range spectroscopy). The present invention meets this need by providing novel methods and devices for use in a high-frequency spectroscopic system enabling to improve signal to noise ratio of the system operation.

The main idea of the invention consists of providing a desired (e.g. desirably high) frequency difference between responding radiation coming from a sample under inspection and reference radiation when both simultaneously arrive to an antenna receiving unit. To this end, the invention takes an advantage of frequency sweeping that is to be used in spectroscopy. This is associated with the following:

In spectroscopy applications it is common to sweep monotonically the frequency of the emitted radiation across a certain desired frequency range. As indicated above, in cases where two or more laser beams are used for generating a high frequency (THz range) radiation (e.g. by photomixing), frequency sweeping is carried out by sweeping the frequency output of at least one laser source, or both of them in a predefined rate(s).

Spectroscopic measurements in the THz regime are performed by irradiating an inspected object with THz radiation and detecting a THz radiation response from the object. In the following description, the THz radiation irradiating the sample/object is referred to as inspecting radiation, while the part of the inspecting radiation reflected from or transmitted through the object and detected by the detector/receiver is sometimes referred to as responding radiation. As indicated above, typical detection devices for THz spectroscopy use homodyne detection in which the responding radiation from the object (sample) is mixed with a reference radiation, which has properties corresponding to the inspecting radiation to generate a detection signal (e.g. an electric/electromagnetic signal). The reference radiation may be for example a radiation portion, sourced together with the inspecting radiation having similar properties, and transmitted directly to the receiver/detector (not through the inspected object/sample). The detection signal generated by the mixing of the reference radiation and the responding radiation can be more conveniently processed as it has a lower frequency than that of the responding radiation. This enables determination of the spectral properties, determining physical and/or chemical properties/conditions of the object, from amplitude and phase measurements, as being functions of frequency of the inspecting radiation, based on detection of the responding radiation.

Thus, the homodyne detection is based on that the reference signal and the inspecting radiation for irradiating the object are originated by the same source(s). Reference radiation may be generated in the transmitter by splitting the laser output, bearing the beat frequency signal, into two portions. One portion is then used for generation of inspecting THz radiation and the other for creation of the reference signal with which to coherently detect the responding radiation.

Generally, at the detector, the instantaneous frequencies of the reference radiation and the inspecting radiation arriving as response from the object/sample are different. This is because of the frequency sweeping carried out in the THz generator (emitter), and because of a time delay between the arrivals to the detector of the responding radiation (radiation response from the object) and the reference radiation the origination of which have been concurrently initiated at the emitter (i.e. have the shared laser source). This time delay may, for example, be a result of different propagation path lengths traversed by the inspecting and reference radiation components to the receiver, and is also associated with a delay in transit of the inspecting/responding radiation due to interaction with the sample. After mixing of the responding radiation with the reference radiation (homodyne detection), and possibly also after suitable band pass filtering, the resultant detection signal has an intermediate frequency component, which is of the order of the frequency difference between the responding and reference signals and typically has (according to the conventional techniques) low frequencies centered around zero frequency.

It should be noted here that for the purposes of the present application the terms intermediate frequency, intermediate frequency component and homodyne frequency used herein generally refer to the frequency of a signal resulted from mixing of the detected signal from the sample with the reference signal/radiation. Also, is should be noted that, differently from typical homodyne detection systems, in which such intermediate frequencies are generally centered around the zero value, the homodyne detection effect utilized in the invention provides for intermediate frequencies which are not centered around zero Hertz value and which therefore are less affected by noise effects such as the "flicker noise".

Let us consider for example the use of a THz generator having substantially constant frequency sweeping rate $\beta$ for generating the inspecting and reference radiation. Here, $\beta$ is the time derivative of the frequency of the transmitted THz radiation in cycles per second per second, and is also referred to herein as frequency variation rate. For such THz generator, a frequency difference between the detected response radiation and the reference radiation is given by $\beta \cdot \tau$ ($\tau$ being the time lag between the receipt of the reference radiation and the response radiation at the detector). In typical THz spectroscopy, $\beta$ may be of the order of 1 THz/sec and $\tau$ may be of the order of nanoseconds. Accordingly, in this example the frequency difference is 1 kHz per nanosecond, i.e. 1 THz/sec. According to the conventional techniques, this frequency offset effect is compensated by adjusting the reference and inspection/response path lengths (e.g. through controlled delay of the reference radiation component) so that the differential delay is artificially calibrated to zero ($\tau=0$).

As an alternative to adjusting the delay to zero, the spectroscopy may be accomplished by step-wise excursion of the interrogating frequency (frequency of the radiation produced by the system, i.e. inspecting and reference), rather than continuous scanning. In this implementation, the frequency is held constant (i.e. $\beta=0$) during a measurement interval. However, this constraint imposes quantization on the frequency variable which may be undesirable when searching for fine-grain features in the spectral response. In addition, operating in discrete (step wise) frequency methodology, a fairly long transient time for frequency settling is generally required at each frequency step which contributes to a substantial increase in the time required for a spectroscopic measurement of a sample.

The present invention provides for resolving this deficiency, so that there is neither a need to match time delays in the arrival of reference and interrogation/responding signals to the receiver (controlling the optical paths), as compared to the conventional techniques (e.g. described in U.S. Pat. No. 7,551,269, nor a need to constrain the method of scanning. The invention permits the use of continuous scanning, while facilitates fast scanning and removes the need to match delay paths.

The present invention also provides for exploiting the coupling between frequency change rate and delay to enhance the measurement quality. This is achieved by providing higher sweeping rate beyond that needed for basic spectroscopy.

In order to allow accurate spectroscopic measurements/detection, the frequency (and possibly also the phase) of the reference radiation, which is mixed with the radiation response, should correspond to the THz frequency from the THz transmitter. Accordingly, the reference signal and inspecting radiation for irradiating the object are originated by the same light source; the output of the light source (laser based light source) is split into two portions. The first portion is used to generate THz range radiation which is directed to propagate to the detector via the interaction with the sample. The second portion is utilized for producing/transmitting reference radiation directly to the detector.

According to the invention, at the detector, the instantaneous frequencies of the reference radiation and the inspecting radiation arriving as response from the object are different. This is because of the frequency sweeping carried out in the THz generator (emitter), and because the path lengths of the inspecting and reference radiation components need not be adjusted to reduce a time delay between their arrivals to the detector. Accordingly, the inspecting radiation (radiation response from the object) and the reference radiation components that concurrently arrive at the detector are those that had been originated/initiated at the emitter at different times, and therefore have different frequencies due to the frequency sweeping carried out in the emitter. This time delay results from the different optical path lengths traversed by the reference radiation and the inspecting radiation interacting with the sample. After mixing of the inspecting radiation with the reference radiation (homodyne detection), and possibly also after suitable filtering, the resultant detection signal has an intermediate frequency component of the order of the frequency difference between the inspecting and reference signals which is in turn proportional to both the time delay and the frequency sweeping rate.

Turning back to the example above and considering a THz generator with frequency sweeping rate β of the order of 1 THz/sec and a time lag τ of the order of nanoseconds between the arrivals of inspecting and reference radiation components at the detector, the frequency of the detection signal (the beat frequency obtained after mixing the inspecting and reference radiation), is of the order of several KHz, e.g. 5-100 KHz.

It is desired to increase the frequency difference (i.e. the intermediate frequency) between the reference and inspecting radiation components simultaneously arriving to the detector, such that a higher homodyne frequency (i.e. intermediate frequency) is obtained. This is because using larger frequency difference allows higher signal to noise in the detection signal and because the noise density (flicker noise) is smaller for higher frequencies.

Moreover, higher intermediate frequencies are also desired since they allow improved range discrimination (higher range resolution/depth resolution) of the sample. The range resolution that can be obtained by spectroscopic detection is given by $$\text{resolution} = \frac{c}{2\beta * \tau},$$

where c is the speed of light, τ is a time delay between the reference and inspecting radiation arriving at the detector and β is the frequency sweeping rate. Improving the range discrimination enables better filtration out of noise and sporadic radiation, such as reflections, from the detection signal, thus also enabling to increase the signal to noise of the spectroscopic inspection. With regard to depth profiling application of this invention, it should be noted that in order to get a phase reference (i.e. a location inside the sample corresponding to the detected response), the free space path is appropriately calibrated prior to actual measurements. The present invention is based on the understanding that increasing the frequencies of the detection signal (i.e. a frequency difference between the frequencies of the reference and responding radiations at the receiver) can be achieved by varying/increasing either the difference between the optical path lengths traversed by the reference and inspection radiations until arriving at the detector (thus varying the time lag between the arrivals of said radiations at the detector), or by increasing the frequency sweeping rate β of the THz generator. According to the invention, increasing the frequency difference between the reference and inspection radiation is achieved by providing an optical drive module which is adapted for fast wavelength sweeping of one or both of the DFB lasers facilitating to achieve higher frequency sweeping rates of the THz generator.

As noted above, THz emitters (radiation generators) typically include an optical drive associated with two or more lasers. THz radiation is generated by photomixing of the output beams from the two or more lasers such that THz radiation has a continuous wave (CW) form with the frequency equal to the beat frequency (frequency difference) of the lasers' output beams. Typically, at least one of the lasers is a DFB laser and thus a control over the frequency of the THz radiation, needed for spectroscopic applications, may be achieved inter alia by utilizing thermo-electric-cooling (TEC) systems for adjusting/controlling the temperature and thus output wavelength(s) said at least one laser. In this manner, the frequency of the output THz radiation can be swept continuously by gradually changing the operating temperature of said at least one laser (more specifically by changing the temperature of the active region of the laser diode, e.g. substantially linearly with time). In many cases, the wavelengths of two DFB lasers of the optical drive are swept in opposite directions, e.g. by heating one laser while cooling the other, thus increasing the rate of sweeping of the THz output frequency and the overall frequency sweeping range.

Hence, according to the conventional approach, the frequency sweeping rate β is strongly dependent on the heat pumping rates of the TEC systems and also on the coupling of such TEC systems with the active region of the laser diodes. Changing the temperature of a laser is a relatively slow process which rate is limited by the ability of the TEC systems to pump heat from the active region of the laser diode (which is small relatively to the TEC system). This, in turn, practically limits the frequency sweeping rate β up to the order of 1 (THz/Sec) even when good TEC systems are used.

According to the invention, sweeping of the laser(s)' wavelength/frequency may be performed by utilizing temperature variations of the lasers active region as well as by varying/modulating other operational parameters of the optical drive (or of the lasers) to obtain frequency modulated continuous wave (FMCW) output signal/light-beam from the optical drive. The frequency (the baseline) of the signal is swept gradually by the temperature variation while the frequency modulation can be achieved for example by modulating the current through the laser diode to affect its output wavelength or by utilizing electro-optical in the path of the output beam of the laser for modulating its wavelength.

Indeed, the common techniques for exercising variation of the output wavelength of a light source/laser include controlling/adjustment of the temperature and/or the current of the light source. However, it should be noted that some aspects of the invention, and specifically those aspects relating to the utilization of fast frequency sweeping rates for the purpose of reducing measurement noise or improving the range resolution (depth resolution), are not limited to the specific technique by which fast frequency sweeping rates are obtained. Accordingly, other techniques, which are currently known or which will be applicable in the future, for varying the output wavelength/frequency of light source might also be used for implementing the technique of the present invention and providing high rate frequency sweeping and/or modulated frequency sweeping without departing from the scope of the present invention.

Thus, according to one broad aspect of the invention, there is provided a method for use in spectroscopic measurements of a sample. the method comprising: generating inspecting and reference electro-magnetic radiation components of substantially the same frequency contents being swept according to a predetermined frequency pattern, directing said inspecting and reference radiation components to a detector along first and second different paths respectively, the sample being located in the first path (allowing interaction of the inspecting radiation component with a sample) to thereby induce a frequency difference (e.g. a predetermined frequency difference) between a frequency of the inspecting radiation component and the reference radiation component interacting at the detector. A signal resulting from the interaction between the inspecting and reference radiation components is thus indicative of one or more properties of the sample at a location where the inspecting radiation interacts with the sample.

According to some embodiments of the invention the frequency difference between a frequency of the inspecting radiation component and the reference radiation component interacting at the detector, is induced by controlling at least one of the predetermined pattern and the propagation of the inspecting and reference radiation components to the detector. Also, the predetermined frequency pattern may be selected in order to provide at least one of the following: (i) the frequency difference between the reference and inspecting radiation component at the detector, being highly sensitive to a difference between said first and second paths thereby increasing spatial resolution of detection of a depth location of the interaction between the inspecting radiation component and the sample; and (ii) the frequency difference between the reference and inspecting radiation component at the detector, being within a certain frequency range thereby increasing signal to noise ratio of detection of said one or more properties of the sample.

Preferably, at least one of the inspecting and reference optical radiation components is formed by one or more pairs of interacting light beams. The frequency of the at least one respective radiation component is thus a beat frequency of said interaction.

The controlling of the propagation of the inspecting and reference radiation components to the detector is such as to allow free propagation of the reference radiation component to the detector (namely propagation independent of a propagation time of the inspecting radiation to the detector), thereby inducing said predetermined frequency difference and enabling to desirably increase said frequency difference to thereby increasing signal to noise of the measurements.

The controlling of the pattern of the beat frequency sweeping comprises concurrently affecting a first, global frequency sweeping rate during a certain time period and a local modulation of the frequency sweeping with a second higher sweeping rate.

According to another broad aspect of the invention, there is provided a method for electromagnetic frequency sweeping of output light from a light source comprising one or more laser diodes, the method comprising: gradually changing an operational temperature of an active region of at least one laser diode thereby causing a substantially monotonic change in the frequency output of the laser diode; and concurrently modulating an electric current through at least one of the laser diodes thereby inducing additional frequency sweeping pattern in the frequency output of the laser diode.

Preferably, a first characteristic time scale of said monotonic change in the frequency output is longer than a second characteristic time scale of the frequency modulation. The frequency modulation thereby presents a sequence of local changes in the frequency output during a global change corresponding to said monotonic change in the frequency output.

According to another broad aspect of the invention, there is provided a method for use in frequency modulated continuous wave (FMCW) spectroscopy, the method comprising producing FMCW electromagnetic radiation by interacting light beam output from at least two laser diodes and gradually changing an operational temperature of an active region of at least one of said laser diodes thereby causing a substantially monotonic change in the frequency output of said at least one laser diode and concurrently modulating an electric current through at least one of the laser diodes for inducing a frequency modulation in the frequency output of the laser diode, thereby increasing a span of frequency gradient of said electromagnetic radiation during the measurements allowing higher signal-to-noise ratio of the measurements.

An operative frequency of the FMCW spectroscopy may be in a THz regime. The interaction of the light beams from said at least two laser diodes generates at least one FMCW electromagnetic radiation beam in a near THz frequency range.

More specifically, in some embodiments of the invention, the method includes: (i) irradiating the sample with an incident beam being a first THz-range FMCW beam to cause a THz radiation response of the sample; (ii) causing an interaction between the response beam of the sample and a certain reference beam being a second THz-range FMCW beam time shifted from the corresponding first FMCW beam, and (iii) detecting an electromagnetic signal resulting from said interaction and having a frequency corresponding to the time shift between the first and second beams and to said frequency modulation of the laser diode.

Generation of the at least one FMCW electromagnetic radiation beam in a THz frequency range utilizes generation of said incident and reference beams, while performing continuous frequency sweeping with certain sweeping rate $\beta$. The parameter $\beta$ is controlled by temperature variation of at least one of the lasers or by current modulation induced in at least one of the lasers, or preferably by combination of both the temperature and current variations. Temperature variation is a relatively slow process, while the current modulation, which may be achieved at electronic speeds, is a quicker one. For example, the scale factor pertaining to temperature controlled frequency variation applied to a laser with wavelength of about 800 nm is approximately 30 GHz/deg.K. Utilizing the electric current modulation, the scale factor relating frequency variation to laser drive current is approximately 1.6 Ghz per mA.

According to the invention, "slow" temperature variation may be used for spectroscopic coverage, while fast current modulation may be used simultaneously to on the one hand improve the radial resolution (depth resolution) of the spectroscopic measurements beyond that achievable with slow frequency sweeping rates (e.g. utilizing frequency sweeping based temperature control alone), and on the other hand improve the signal to noise of the measurement due to higher intermediate homodyne frequency. In this case the laser will be driven by modulated current waveform (e.g. sinusoidal/saw-tooth/triangular etc'), while the temperature may be varied simultaneously in a linear fashion.

According to yet further broad aspect of the invention, there is provided a method for use in spectroscopic measurements of a sample, the method comprising: generating inspecting and reference radiation components corresponding to respectively first and second pairs of light beams of the same beat frequency contents being swept according to a predetermined pattern and directing said inspecting and reference radiation components to a detector along first and second different paths, the sample being located in the first path, said pattern being selected so as to induce a desired frequency difference between a frequency of the inspecting radiation component and the reference radiation component interacting at the detector.

The invention also provides a spectroscopic measurement method comprising: generating inspecting and reference radiation components corresponding to respectively first and second pairs of light beams of the same beat frequency contents being swept with a certain sweeping rate, and directing said inspecting radiation component to propagate to a detector along a first path passing through a sample and directing the reference radiation component to the detector along a second path, the first and second paths being such that the inspecting and reference radiation components interacting at the detector correspond to light beam pairs generated at different times thereby inducing a desired frequency difference between the interacting inspecting and reference radiation components.

According to yet another aspect of the invention, there is provided a system for use in spectroscopic measurements of a sample, the system comprising: a radiation transmitter unit configured and operable for generating inspecting and reference electro-magnetic radiation components (e.g. optical or quasi-optical or THz range radiation) of substantially the same frequency contents, and for sweeping said frequency according to a predetermined frequency pattern; and a detector located in a first path of the inspecting radiation components after passing through a sample and in a second path of the reference radiation component directly propagating from the transmitter unit to thereby induce a frequency difference (e.g. being predetermined difference) between a frequency of the inspecting radiation component and the reference radiation component interacting at the detector, a signal resulting of interaction between said inspecting and reference components being indicative of one or more properties of the sample at a location where said inspecting radiation interacts with the sample.

According to some embodiments of the invention the system is configured to adjust/tune/control the frequency difference between the components of the inspecting and the reference radiation at the detector, by controlling at least one of the predetermined frequency pattern and the propagation of the inspecting and reference radiation components to the detector. Additionally or alternatively the predetermined frequency pattern may be selected such that the frequency difference, between the inspecting and reference radiation components at the detector, is highly sensitive to a difference between the first and second paths (thereby increasing spatial resolution of detection of a depth location of the sample portion being inspected) and/or it is within a certain frequency range which is selected in order to increase the signal to noise ratio of detection of one or more properties of the sample.

According to yet another broad aspect of the invention there is provided a system for sweeping of the output frequency of a light source comprising one or more laser diodes, the system comprising:

a frequency sweeping module adapted for affecting gradual change of one or more operational parameters of a light source to thereby cause gradual sweeping of the frequency of the light source across a certain frequency range; and a frequency modulation module adapted for modulating one or more operational parameters of the light source to induce modulation in the frequency of light source.

Said one or more laser diodes may comprise one or more DFB lasers; and said gradual change of said one or more operational parameters may comprises a gradual change of the operational temperature of an active region of at least one DFB laser affecting substantially monotonic sweeping of the frequency of said at least one DFB laser. The frequency sweeping module may comprise at least one temperature control unit connectable with at least one TEC system thermally coupled with said at least one DFB laser; said temperature control unit is configured and operable for controlling the operation said at least one TEC system.

The frequency modulation module may comprising at least one current control unit connectable to at least one laser diode and configured and operable for modulating an electric current flowing through said at least one laser diode to thereby induce modulation in the frequency of said at least one laser diode.

Output radiation from said light source may be obtained by coupling light beams from said one or more laser diodes. The light source may comprise two laser diodes and the frequency sweeping module may include at least one temperature control unit. For example, two temperature control units may be used and may be associated respectively with two laser diodes; the frequency sweeping module is adapted in such case to operate said two temperature control units to change the temperatures of the laser diodes in opposite directions.

The frequency modulation module may also include one or more current control units associated with at least one of the laser diodes. For example, two current control units associated respectively with two laser diodes. The frequency modulation module may be adapted to operate said two current control units to modulate the currents through the respective laser diodes in opposite directions.

As indicated above, in some embodiments of the invention, a first characteristic frequency variation rate in the output frequency of the light source obtained by operating said frequency sweeping module is lower than a second characteristic frequency variation rate obtained by operating said frequency modulation module. The modulation in the frequency of light source thus presents a sequence of local changes in the frequency output during a global change corresponding to said gradual sweeping in the frequency output.

The invention in its yet another aspect provides a high-frequency spectroscopy system, the system comprising:

a radiation generator for generating an inspecting radiation and a reference radiation of the same properties;

a frequency sweeping module associated with said radiation generator for inducing frequency modulation in said inspecting and reference radiation components, said frequency modulation having a global frequency sweeping rate and a local frequency sweeping rate corresponding to desired frequency and radial resolution to be obtained in a spectroscopic measurement.

Such system comprises or is connectable to a radiation receiver unit configured and operable for mixing the reference radiation component and a responding radiation component being a reflection or transmission of the inspecting radiation component from or through the sample. The receiver unit is configured and operable for determining a frequency difference between the reference and responding radiation components being mixed and utilizing said local frequency sweeping rate to identify a in-depth location, at said radial resolution of a sample, associated with said received responding signal.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 1 shows an example of an antenna system, for use in spectroscopy according to the conventional approach;

FIG. 2 illustrates noise density characteristics of an amplifier which corresponds to the flicker noise effect;

FIG. 5A shows the THz frequency sweeping obtained by changing the temperature of the light source from which the THz radiation is generated, and FIG. 5B is a time profile of FMCW radiation obtained according to the invention by sweeping the THz frequency while changing both the temperature and the current of the light source.

DETAILED DESCRIPTION OF EMBODIMENTS

Figure 3:
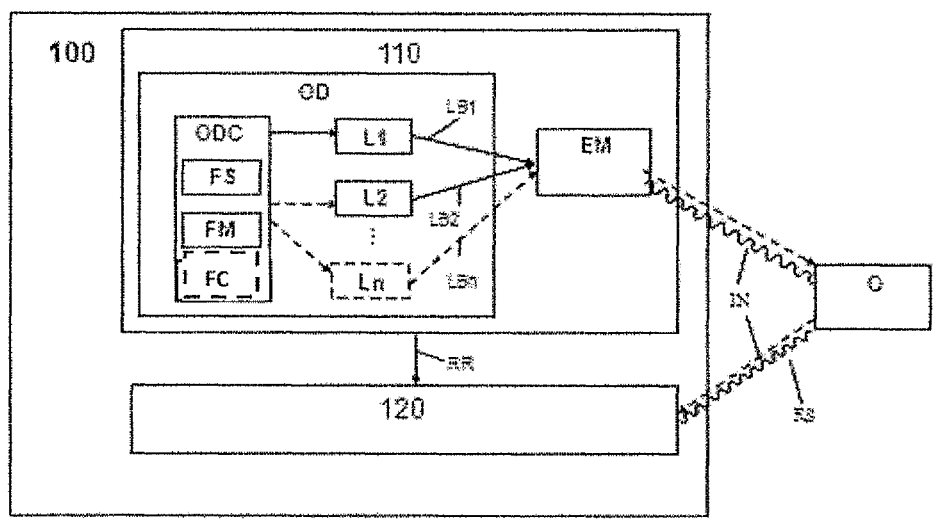
FIG. 3 illustrates schematically a THz spectroscopy module according to the invention.

Reference is made to FIG. 3 illustrating an example of a THz transceiver 100 according to an embodiment of the present invention including a THz transmitter 110 and a detector (receiver) 120. In the present example, the transceiver 100 is configured and operable for carrying out accurate spectroscopic measurements of a sample/object in the THz frequency regime. The THz transmitter 110 is adapted to generate THz radiation with high frequency-sweeping rates $\beta$, and to transmit at least a part of this THz radiation, inspecting radiation IN, towards the object/sample O under inspection, and reference radiation RR towards the THz detector. The THz detector 120 is capable of receiving and detecting high-frequency modulated signals, being therefore capable of exploiting the high frequency-sweeping rate $\beta$ for generating a detection signal HS (e.g. homodyne signal) of relatively high frequencies indicative of the response radiation RS emanating from/through the object in response to its irradiation. The relatively high frequencies of the signal HS result with high signal to noise ratio and with improved range resolution of the spectroscopic measurements.

The THz transmitter 110 includes an optical drive (light source system) OD and a THz emitter EM optically coupled thereto. The THz emitter EM is configured and operable for generating THz radiation by mixing input light beams, which are light signals emanating from the optical drive OD. The optical drive includes at least two light sources, generally designated $L_1$-$L_n$, which may be light emitting elements themselves or light input ports associated with remotely located light emitting elements (e.g. via optical fibers), and also includes an optical drive controller ODC. The optical drive OD is configured and operable to generate at least two light beams, $LB_1$ and $LB_2$ (typically in the IR wavelength range), which are directed onto an active region of the THz emitter EM (which serves as a photomixer), and thus generate an electric current/EM-field in the THz band.

The optical drive controller ODC is configured and operable for controlling the operational parameters of at least one light source (e.g. $L_1$ or $L_2$) such as to allow high rate wavelength sweeping of the at least one output light beam (e.g. $LB_1$ or $LB_2$). Utilizing the optical drive controller ODC, the transmitter 110 is capable of sweeping the frequency of the transmitted radiation with high frequency-sweeping rate $\beta$ and across a desired THz frequency range suitable for spectroscopic measurements.

Detector 120 is configured for receiving and detecting (e.g. homodyne detection) of the radiation response RS by utilizing mixing of the radiation response RS with reference radiation RR which is received from the transmitter 110 (e.g. directly). As a result of such mixing, an output (homodyne/intermediate) signal is generated, by the detector, containing intermediate frequencies of the differences between the frequencies of the mixed reference radiation RR and radiation response RS.

As noted above, with the conventional approach for executing frequency sweeping of the laser diode output, i.e. by temperature changes of the active region of the diode, it is impractical to provide a constant high sweeping rate $\beta$ of the high-frequency signal across the full frequency range of THz spectroscopy. However, performing THz spectroscopy with high frequency sweeping rates $\beta$ would be advantageous in terms of measurement/detection accuracy.

The present invention provides a solution for the above by utilizing a first, substantially steady/monotonic sweeping of the THz radiation with a frequency sweeping rate $\beta_0$ and utilizing a second modulated sweeping with higher rate $\beta_1$. Thus, according to the invention an effective modulated frequency sweeping rate $\beta$ can be obtained for example in the form of $$\beta = \beta_0 + \beta_1(t)$$

where t is a time parameter, $\beta_1(t)$ is the sweeping rate which is a non-linear function of time to generate desired sweep rate alternation during said monotonic sweeping with the rate $\beta_0$.

This can be achieved by configuring the optical drive controller ODC with the ability to apply a monotonic/constant wavelength sweeping rate to one or more of the light sources $L_1$-$L_n$ and to apply an additional, modulated wavelength sweeping to at least one of the light sources, which may be the same or different from said at least one light source. To this end, the optical drive controller ODC includes a frequency sweeping controller FS configured to induce a first monotonic sweeping of the output wavelength from one or more of the light sources $L_1$-$L_n$ by controlling at least some of their operating parameters and a frequency modulation controller FM affecting a modulation of the output beam wavelength of (said) one or more of the light sources $L_1$-$L_n$ by controlling the same or different parameters of their operation. It should be noted that the operating parameter(s) of the light source to be controlled may be that of the light emitter itself or of the light input port and/or associated light guide (generally light propagation media).

As noted above, the transmitter is configured and operable for generating reference radiation RR and transmitting it towards the detector. The reference radiation RR is mixed at the detector with the radiation response RS from the object which results in the detector output signal HS (being the homodyne/intermediate frequency signal).

The reference radiation RR typically includes a portion of the light beam(s) emerging from the optical drive OD. Reference and inspecting radiation portions are obtained by splitting the light beams from the optical drive OD into the reference radiation portion and the inspecting radiation portion and directing the reference portion to the detector 120 and the inspecting radiation portion towards the emitter. In this case, THz frequency electric field (i.e. reference oscillator) is generated at the detector 120 by mixing the light beams of the reference radiation portion.

Generally the reference radiation RR and the inspecting radiation IN are sourced concurrently from the same origin (e.g. by light beams from the optical driver OD or THz radiation from the emitter EM). Accordingly, at the time these radiations are generated/emitted from the transmitter 110, they are associated with similar THz content (frequencies/modes). It should be understood that THz content refers to the frequencies/modes and possibly also the respective intensities which are included in the reference RR and in the inspecting IN radiation or which can be generated therefrom, e.g. by mixing.

However, the portions of the inspecting IN and reference RR radiation which arrive concurrently to the detector 120, correspond to light beams originated at different times from the transmitter 120 and are thus associated with different THz content (i.e. because there may be a time delay $\tau$ between arrivals of concurrently generated beams at the transmitter due to a difference $\Delta R$ in the length of their optical path to the detector). This different THz content of the inspecting IN and reference RR radiation gives rise (or at least increases) the frequencies of the output signal HS which is obtained after mixing of those radiations at the detector.

The difference in the frequency contents of the reference RR and inspecting IN radiations, and accordingly the frequency of the output signal HS, is of the order of the frequency sweeping rate $\beta$ multiplied by the time delay $\tau$, i.e. $\sim\beta\cdot\tau$. Frequency sweep due to temperature variation is fairly coarse and achieves relatively big frequency change over the temperature range but fairly slow. Considering frequency sweeping rates $\beta_0$ of this order and considering a difference $\Delta R$ between the optical paths of the reference RR and inspecting IN radiation of about few meters (the inspecting radiation IN propagates 1 m from the transmitter 110 to the object O and 1 m from the object O to the detector 120 while the reference radiation RR propagates a negligible distance), a time delay $\tau$ of a few nanoseconds is obtained between the reference RR and inspecting IN radiation and accordingly frequencies of the order of tens of KHz are obtained in the output signal.

As noted above, accurate spectroscopic measurement, namely having high SNR in the output signal HS and/or high range resolution of the measurements, can be obtained when the output (homodyne) signal HS is of relatively high output frequencies, e.g. in the range of hundreds of KHz and up to few MHz and above. The optical drive controller ODC of the invention facilitates high sweeping rates $\beta$ of the THz radiation from the transmitter by controlling/modulating one or more operational parameters of the light sources $L_1$-$L_2$ such as their operating current and temperatures. As a result, an output signal HS of higher intermediate frequencies can be generated at the detector, and thus accurate spectroscopic measurements in the THz regime can be obtained. This will be described more specifically further below.

Generally, conventional DFB lasers have frequency coverage of about 1.5 THz (the output frequency of the laser can be swept by about 1.5 THz). Accordingly, photomixing the output light beams from two DFB lasers allows generating THz radiation which can be swept to cover a range of about 3 THz.

According to the invention, more than two light sources/lasers might be effectively utilized for providing spectroscopic measurements with broad frequency coverage in the THz regime. In this case, at least two of the multiple lasers have different frequency output ranges. By photomixing different pairs of lasers (e.g. successively) while sweeping the output frequencies of each photomixed pair, different frequency ranges in the THz regime can be covered thus providing a broader total frequency coverage.

In the embodiment of the invention illustrated in FIG. 3, an optional frequency coverage controller FC is included being configured and operable for selecting and operating different pairs of the light sources L1-Ln successively, resulting in different beat frequencies. Those different beat frequencies are then swept by the utilizing at least one of the frequency sweeping and frequency modulation controllers to cover different THz ranges (optionally complementary ranges) thereby allowing THz spectroscopy within a broad frequency/spectral range.

For example, utilizing three DFB lasers, photomixing of the first and second lasers can be used to sweep the beat frequency (i.e. the THz frequency) within a first THz range which may be about 3 THz wide. Then, the first laser may be photomixed with a third laser, having output frequency range different from the second laser, and thus the resulting beat frequency can be swept within a second THz range different from the first THz range (first and second ranges being possibly complementary ranges). As also the second range may have width of up to about 3 THz, total frequency coverage in the THZ regime of about 6 THz can be obtained. Even broader frequency coverage can be obtained for example by utilizing additional lasers (more than three) and by coupling different pairs of these lasers at each specific time period to allow sweeping of the beat frequency within multiple THz ranges.

Figure 4:
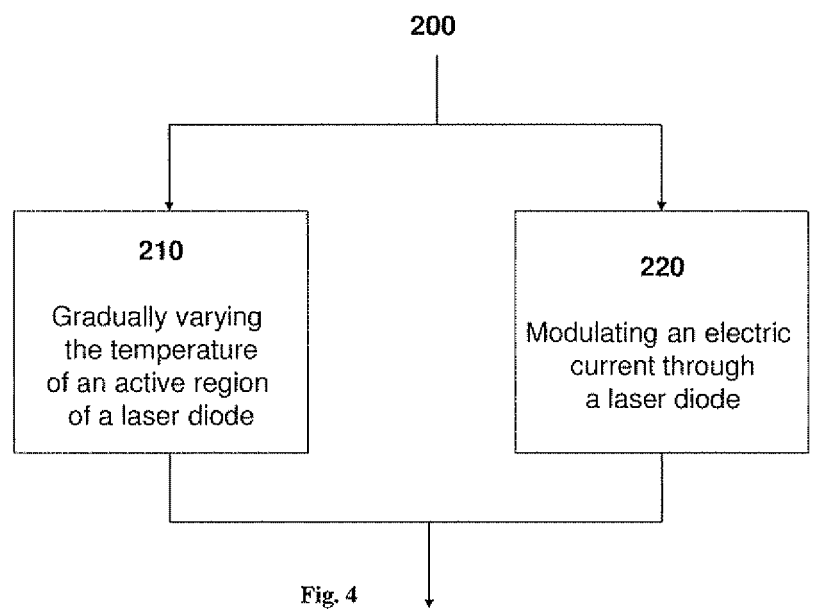
FIG. 4 is a flow diagram of a method according to the invention for sweeping the output wavelength of a light source such as DFB laser.

Reference is made to FIG. 4 exemplifying a flow diagram 200 of a method according to the invention for controlling the operation of one or more laser diodes, such as DFB lasers, to generate an output laser beam with fast variation of its wavelength. The method can be implemented in an optical drive OD (i.e. by the optical drive controller ODC) illustrated in FIG. 3 and can be used to facilitate the generation of frequency modulated continuous wave (FMCW) having high rate of frequency sweeping/variation THz by THz generators/emitters.

Wavelength/frequency sweeping of a laser diode output with high sweeping rates is achieved according to this method by concurrently and/or interchangeably carrying out the following operations:

In a first operation 210, at least one operational parameter of the laser diode, such as its operational temperature (e.g. the temperature of its active region) is controlled (controllably varied) for maintaining continuous sweeping 210 the laser diode wavelength for example for providing a monotonic/steady wavelength sweeping with relatively fixed sweeping rate. With respect to the system of FIG. 3, this operation might be performed by the frequency sweeping controller FS to control the operational temperatures of one or more of the lasers for example by controlling the operation of thermo-electric cooling (TEC) systems (TEC) coupled therewith.

In a second operation 220, the same or other parameter of the laser's operation is controlled for modulating the laser's wavelength in time. This can be for example achieved by applying modulation to the current through the laser diode thus affecting a modulation of its output. With reference to the FIG. 3 this operation might be performed by the frequency modulation controller FM.

By changing the operational temperature of a DFB laser, its output frequency can be changed at a rate of about 1.5 THz/sec. This can be achieved for example by heating/cooling the lasers utilizing a TEC system with high heat pumping rate (for example the TEC system disclosed in a co-pending U.S. application Ser. No. 61/292,649).

Figure 5A:
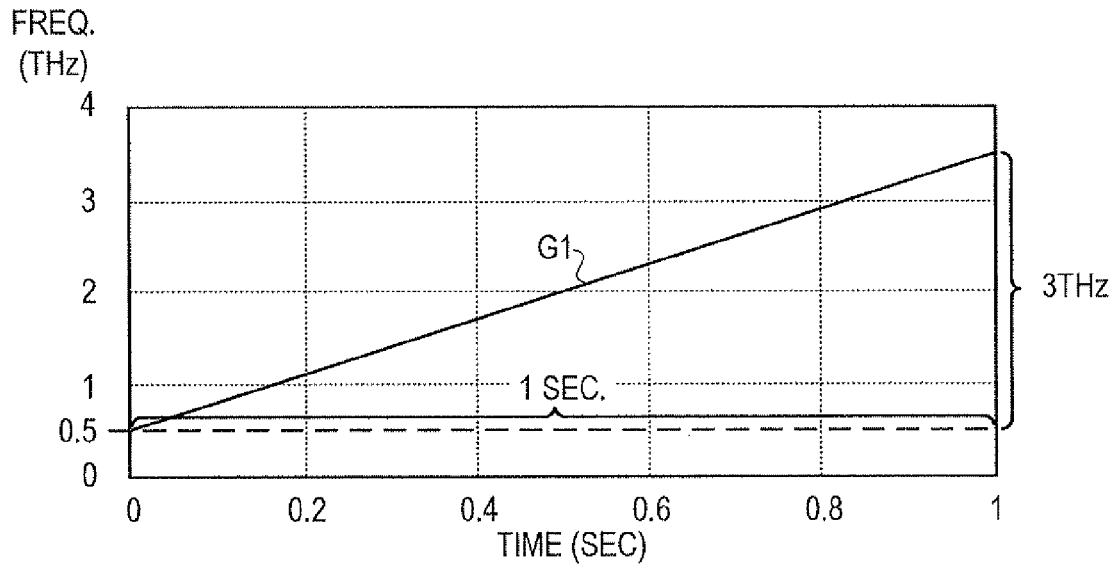
FIGS. 5A and 5B illustrate graphically two time profiles of THz frequency sweeping, where

FIG. 5A illustrates graphically the sweeping of THz radiation frequency as obtained by photomixing of light outputs of two DFB lasers which operational temperatures are changed in time in opposite directions. Graph G1 illustrates the evolution of THz frequency as function of time while sweeping of the THz radiation frequency across a range of about 300 GHz-3.5 THz. The slop of graph G1 designates the sweeping rate β which is substantially constant in this case. Frequency sweeping is obtained by applying heating and cooling respectively to the two DFB lasers (their active regions) such that their wavelengths are swept to opposite directions. Since the temperature variation of the lasers is a gradual and relatively slow process, relatively low frequency sweeping rate $\beta=\sim 3$ THz/sec is obtained.

Turning back to FIG. 4, in order to increase the frequency sweeping rates and to enable accurate spectroscopy measurements, the second operation 220 is carried out for modulating the laser's wavelength in time and thus temporally inducing high frequency sweeping rates of the THz radiation. For example, in addition to the continuous frequency sweeping carried out in the first operation by changing the DFB laser/s temperature, in the second operation the wavelength of one or both of the DFB laser/s is fast modulated by changing the electric current for the laser/s.

The electric current change of the DFB laser has an immediate affect on the lasers' output (as opposed to temperature changes which requires time for cooling/heating the lasers active region) and thus higher frequency modulation rate can be achieved corresponding to wavelength variation rate of up to the order of 100 nm/sec. By exploiting the high wavelength modulation rates in the lasers' output, THz sweeping with frequency sweeping rates of about $\beta=\sim 15$ GHz/milisec can be obtained. This is about ten times higher that the frequency modulation obtained solely by the temperature variation.

However, only a limited variation of about 0.1 nm of the wavelength of the DFB laser is obtained by the change of the electric through the laser, which is insufficient for generating and sweeping across the whole THz frequency range (zone). Thus according to the invention, the temperature variation of the laser diode (e.g. first operation 210) can be used to provide substantially monotonic/constant THz sweeping with typical rates of e.g. $\beta_0=\sim 3$ THz/sec while current modulation is applied (e.g. second step 220) for providing alternating THz sweeping rates in the range of $\beta_0=\sim+/-30$ THz/sec.

It should be understood that applying a fast modulation of the laser wavelength is not limited to tuning/modulation of the electric current through the lasers and it can be performed for example applying additional fast and accurate temperature change/modulation, in addition to the sweeping applied by the temperature. Alternatively or additionally, modulation of the wavelengths of the laser beams can be performed by affecting the optical path of the laser beams for example by utilizing a non-linear optical element along the optical path. To this end, the term operational parameters of the light sources/lasers include also the optical path/medium which the light beams from those light sources traverse. Yet another option is to use a mechanical, optical or any element to frequency-modulate the output beam from the THz emitter.

Figure 5B:
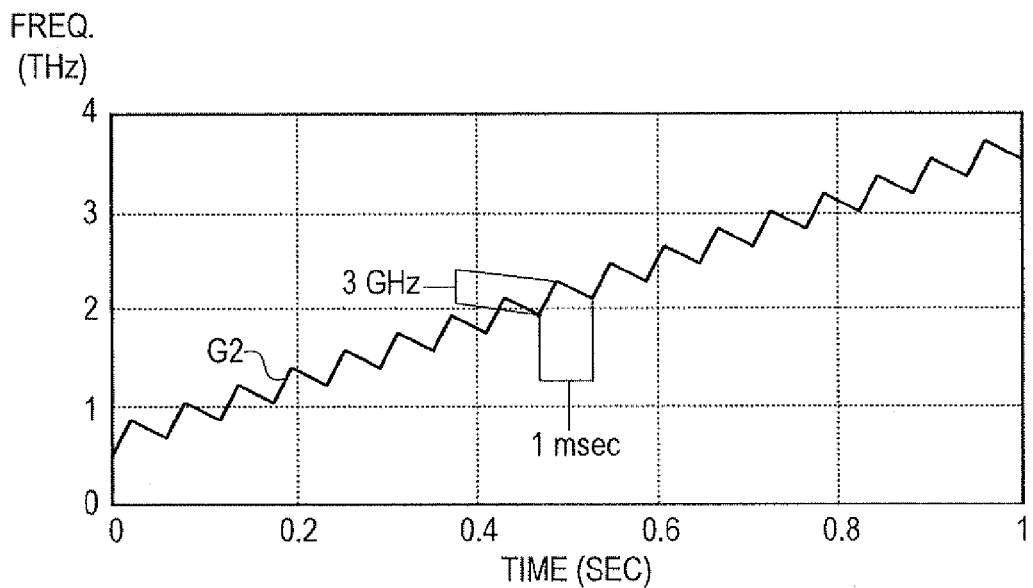

Turning now to FIG. 5B, there is shown a graphic illustration G2 of the THz frequency vs. time as generated utilizing a frequency sweeping technique according to an embodiment of the present invention. In this example the THz frequency is swept from low frequencies to high frequency (or vice versa within frequency sweeping range of about 300 GHz-3.5 THz) using a gradual temperature change while concurrently relatively fast modulation of electric current through the active regions of the lasers is applied. Similarly to the graph G1 of FIG. 5A also here, the gradual temperature change provides monotonic frequency sweeping across the desired THz frequency range with monotonic sweeping rate $\beta_0$ of about ~3 THz/sec. A fast modulation of the frequency with period $t_m$ of about 1 msec and with relatively low frequency shifting amplitude of about 30 GHz is obtained by applying current modulation to the laser diode(s). This results with relatively high frequency weeping rates $\beta_1$ ranging/alternating in between +/−30 THz/sec.

In this example, current modulation if applied to both laser diodes with time shift of about 0.5 msec (i.e. phase shift of about π) between the current modulations such that when relatively high current is flowing through one of the laser diodes, relatively low current flows thorough the other. This results with the output wavelengths of the laser diodes swaying in opposite directions thus increasing the resultant frequency shifting amplitudes. It should be noted however that according to the invention, each of the electric current modulation and the temperature variation can be applied to only one of the laser diodes and not necessarily to the same one.

A comparison of the THz frequency sweeping (and the rates) illustrated in FIGS. 5A and 5B yields the following results: Without frequency modulation (e.g. without modulating the current), and considering time delay τ of about 7 nanoseconds between the reference and inspecting radiations (e.g. corresponding to length difference ΔR of about 2 m between the optical paths of the reference and inspecting radiation between transmitter to the detector) the frequency of the output (homodyne) signal of the detector (e.g. the frequency difference between the reference inspecting radiation) and is about 20 KHz. With frequency modulation, e.g. when current modulation is applied, β approaches 30 GHz/msec and the frequency of the output signal of the detector reaches to about 200 KHz.

Figure 6:
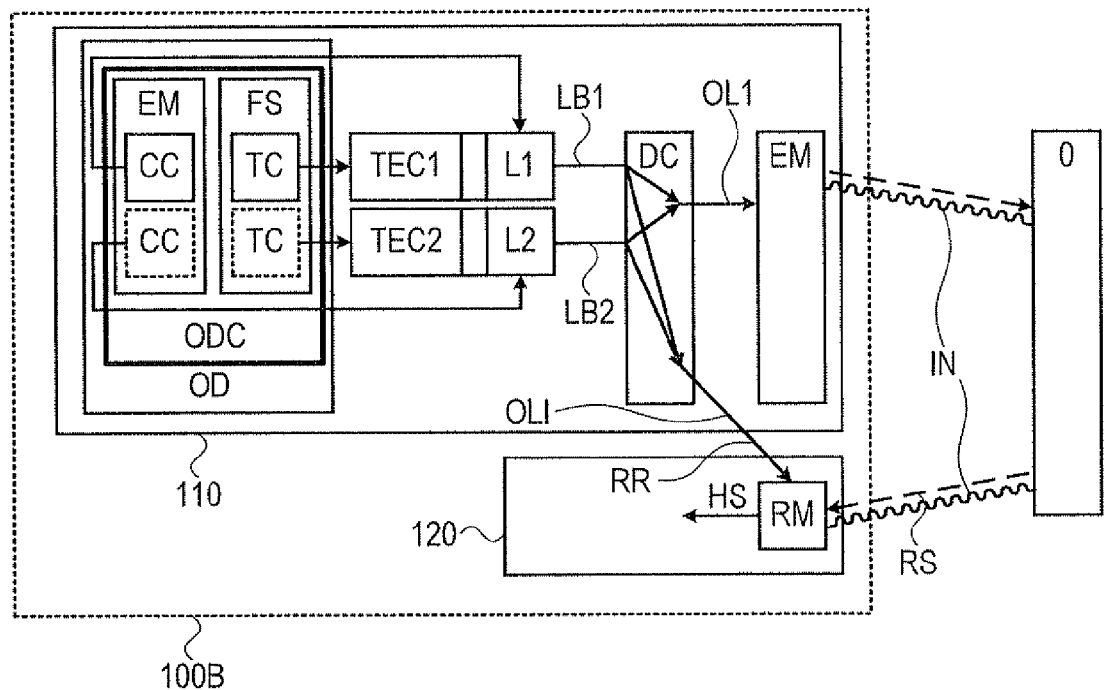
FIG. 6. is an example of a light coupling assembly used in the present invention for receiving and mixing light beams from two lasers and providing two output light beams having substantially similar spectral contents and energy.

Reference is made to FIG. 6 illustrating a more specific, but not limiting example of THz spectroscopic system 100A according to the invention. Similar referenced numbers are used in all the figures to designate common elements having essentially similar functionality or purpose.

System 100A includes a THz transmitter (THz radiation generator) 110 and a detector 120. The radiation generator 110 includes a THz emitter EN and an optical drive OD optically coupled together through an optical coupling OC for generating THz radiation which can be used to irradiate an inspected object O with inspecting radiation IN. The optical drive OD includes, in the present example, two light sources L1 and L2 (DFB lasers) associated with respective thermo-electric cooling systems TEC1 and TEC2 and an optical drive controller ODC connected to the light sources and to the thermo-electric cooling systems. The ODC is configured and operable for controlling the temperatures of—and the electric currents through—the light sources L1 and L2 and to thereby control and vary the wavelength of the lasers' output beams LB1 and LB2 with relatively fast rates. As noted above, this enables sweeping the THz radiation generated, at the emitter EM by photomixing of those light beams, with high frequency sweeping rates β.

To this end, the optical drive controller ODC includes a frequency/wavelength modulation controller unit FM, which in this example include one or more electric current controllers CC(s) connectable to one or more light sources L1 and L2 and configured and operable for modulating the current through the light sources L1 and L2 to affect a modulation of their output wavelengths. The optical drive controller ODC also includes a frequency sweeping controller FS which, in this case, includes one or more temperature control unit TC(s) that are configured and operable for controlling respectively the operation of the thereto-electric cooling systems TEC1 and/or TEC2 and to thereby affect the temperature of lasers L1 and/or L2 and to allow monotonic sweeping of their wavelengths and of the THz radiation obtained by their mixing.

The output light beams LB1 and LB2 from the lasers L1 and L2 are mixed together and optically coupled with at least one THz emitter EM from which the inspecting radiation and possibly also the reference radiation are generated. In many cases, it is preferable that the mixed light beams LB1 and LB2 are split (e.g. by optical coupler OC) into two portions OL1 and OL2, preferably of substantially similar spectral content and energy such that one portion is associated with the generation of the inspecting THz radiation and the other is associated with or is serving as the reference radiation.

As illustrated in the figure, one THz emitter EM may be included in the transmitter 110 for generating the inspecting radiation from one portion OL1 of the mixed light beams while another portion of the light beams OL2 serves as the reference radiation and is transmitted/directed to the detector where it is mixed to generate a reference oscillator.

In general THz emitter EM may include any suitable photomixer which can be coupled with an appropriate THz antenna for generating, in the antenna, electric currents having frequencies in THz regime (being the beat frequency of the two lasers). Known in the art THz emitters utilize photoconductive semiconductors such as GA to generate THz currents or are based on the free-charge-propagation technology (e.g. vacuum based technology) as disclosed for example in WO 2007/132459 assigned to the assignee of the present invention.

Hence the THz generator/transmitter 110 generates and transmits reference radiation RR towards the detector 120 which may include (or be constituted by) a portion e.g. OL2 of the light beams. The detector 120 includes a receiver mixer RM adapted for mixing a response radiation RS from the object O (referred to herein as being a part of the inspecting radiation IN returned from the object to the detector) with a reference radiation RR that is transmitted directly from the THz transmitter 110. The receiver mixer RM is configured for carrying out homodyne detection of the response radiation RS and for generating detection signal HS (intermediate frequency signal) including a beat frequency of the response RS and reference RR radiations. The current modulation applied by frequency modulation controller FM to the laser diode increases the frequency sweeping rate of the transmitter 110 and thus causes the frequency difference at the detector/receiver to increase (compared to the case of no current modulation is applied).

Due to the high frequency sweeping rates $\beta$ provided by the optical drive of the present invention, the detection signal obtained has relatively high intermediate frequencies allowing accurate spectroscopic measurements with relatively high signal to noise ratio over fairly broad spectral range.

Reference is made to FIGS. 7A to 7D illustrating graphically various forms of fast current modulations that can be applied to one or more of the light sources (lasers) of the systems illustrated in FIGS. 3, 6 in order to modulate their output wavelengths.

Figure 7A:
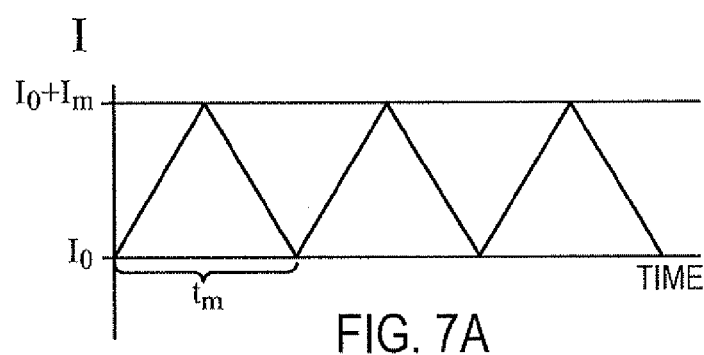
FIGS. 7A to 7D show few examples of possible current modulation schemes which can be used in accordance with the present invention for generating frequency modulated output laser beams.

FIG. 7A exemplifies a triangle current modulation waveform where the current I is periodically increased above certain baseline value $I_0$ by current modulation amplitude $I_m$ and decreased back towards the baseline value $I_0$. In this example and the increase and decrease rates as well as the current modulation period $t_m$ are fixed constants.

Utilizing current modulation, as illustrated in this figure, THz frequency sweeping with rates upto 30 THz/sec can be obtained. For example, current modulation can be used for modulating the frequency of a THz radiation which baseline frequency (with respect to which the frequency modulation is applied) is monotonically swept (e.g. utilizing temperature variation) with rate of about +3 THz/sec. As a result, the frequency sweeping rate $\beta$ of the THz radiation acquires periodic value which may alternate between about +30 THz/sec to −24 THz/sec. Accordingly, the alternating positive and negative high frequency sweeping rates are obtained which can be exploited by the receiver/detector for providing measurements with high signal to noise (e.g. with non-zero intermediate frequencies and therefore with low flicker noise).

Figure 7B:
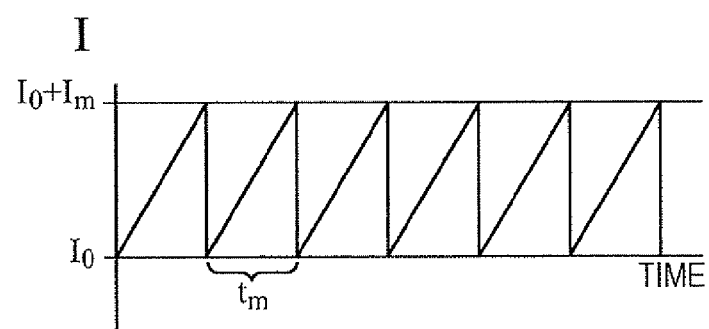
Figure 7C:
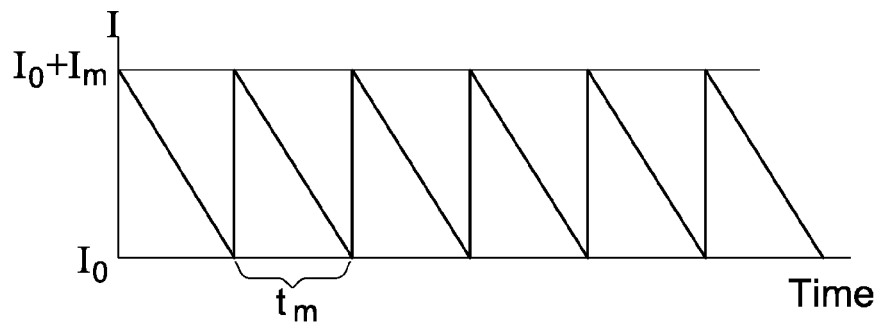
Figure 7D:
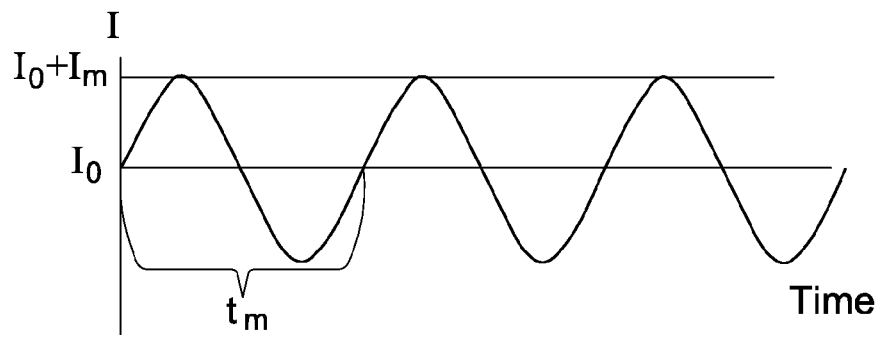

FIGS. 7B and 9C show two examples of saw-tooth current modulation waveforms suited for use in the present invention. In FIG. 9B a periodic increase of the current above a baseline value $I_0$ with certain finite increase rate is followed by abrupt/immediate decrease of the current back to the base line level $I_0$; and vice-versa in FIG. 9C. Such saw-tooth current modulation schemes can be exploited for providing substantially constant and high frequency sweeping rate $\beta$. The sweeping rate $\beta$ obtained is this case may be considered a constant value which is maintained along all the frequency sweeping range except for at "singular" time points (e.g. $t_s$) at which abrupt decrease/increase of the current to the laser diode is applied. Considering the durations of these "singular" time points as being negligible, they may be ignored in the detection module, thus allowing a homodyne detection to be performed as if a non-modulated and high (e.g. ~30 THz/sec) frequency sweeping rate $\beta$ is provided by the THz transmitter.

FIG. 5D 9D illustrates an example of a sinusoidal current modulation of a laser diode with baseline $I_0$ amplitude $I_m$ and period $t_m$.

It should be understood that in accordance with the present invention other modulations of wavelengths of light beams from the optical drive can be applied. For example any other form of current modulation can be used as well as modulating the wavelengths of the optical drive by varying modulating other of its operational parameters such as the temperature of the lasers or operational parameters of other optical/electro-optical means in the path of the laser's beam.

It should be also understood that the disclosed method and systems of the present invention is not limited for THz spectroscopy. The frequency modulated continuous wave FMCW sweeping technique of the invention can be implemented for high frequency sweeping of electromagnetic radiation in various frequency bands including inter-alia UV, visible, IR and microwave. The radiation swept by the FMCW technique of the invention may be that emanating from one light source/port or a radiation that is generated via photomixing of light beams from two or more light sources.

As noted above, according to some embodiments of the present invention, continuous frequency sweeping with high frequency sweeping rates can be effectively used for depth profiling (3D imaging) of a sample. In this connection, the present invention takes advantage of the frequency offset that accrues when a linear frequency scan is used. As indicated above, such frequency offset resulting from a delay in the time of arrival of the responding and reference radiation components to the receiver antenna, typically leads to the flicker noise. However, the invention utilizes this effect, rather than trying to reduce it, based on the understanding of the following.

Figure 8A:
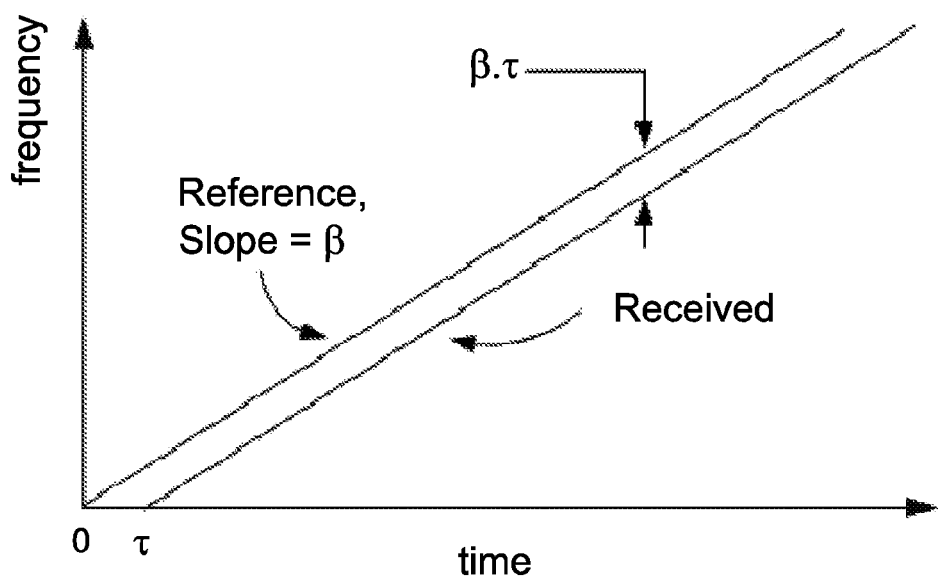
FIGS. 8A to 8C describe the delay-induced frequency offset problem resulting from the conventional approaches illustrated in FIGS. 1, 3 and 4.
Figure 8B:
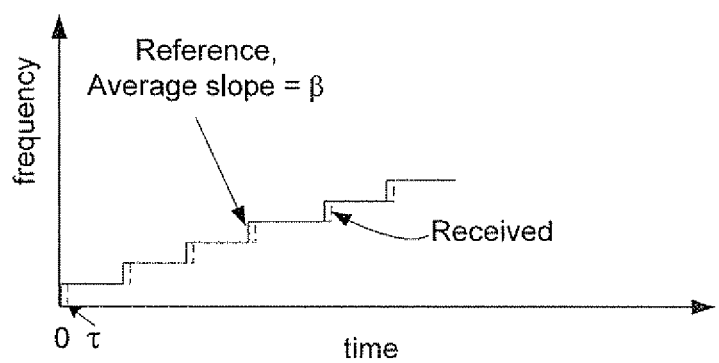
Figure 8C:
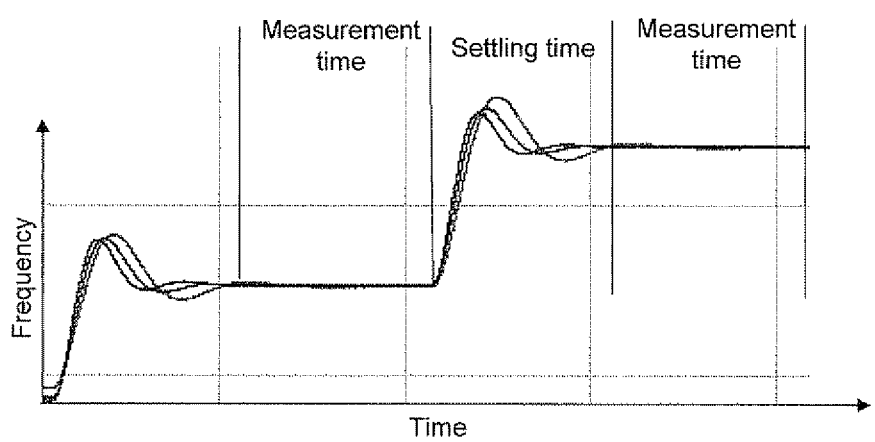

Referring to FIG. 8A, there is shown an effect of frequency scanning onto a frequency off-set. The latter is proportional to a time delay between the reference optical signal in the receiver and the received wave. At a scale factor of 1 kHz per nsec per THz/sec, the frequency offset makes conventional lock-in detection with a band-pass filter ineffective, because the frequency offset means the signal averages to zero, or it can even fall outside the band-pass of the averaging filter. It is not practical to maintain τ=0, if delay is needed for adjusting phase or for delay profiling, so an alternative step-scan method is used as shown in FIG. 8B. This solves the problem, but at the expense of lost time as each step in the frequency profile has to be allowed time to settle. Minimising scanning time is highly advantageous in practical applications. The step-scan approach wastes valuable time because the temperature control loop which is used for frequency tuning of the laser(s) requires appreciable time to settle after a step. A typical practical step response is shown in FIG. 8C which illustrates the wasted time while temperature settles. The time wasted in settling may approach the time available for measurement.

The present invention takes advantage of the frequency offset that accrues when a linear frequency scan is used. In order to obtain practical levels of frequency sweep speed and delay, the frequency offset will naturally lie above the flicker noise of the receiver amplifier. This allows, the response at the natural offset frequency to be measured using Fast Fourier Transform processing. The Fast Fourier Transform implements a contiguous bank of band-pass filters. Depending on sweep rate and delay, the offset frequency will lie within one or a small number of filters (bandwidths). A conventional interpolation algorithm, well known in signal processing, may be used to estimate the signal amplitude over a time interval corresponding to the data collection time of the Fast Fourier Transform. This time interval defines the frequency resolution of the THz measurement in the same way as the frequency jumps in step-scan (as described above with regard to one of the known techniques), but without the settling-time loss.

It is fundamental that the frequency sweep-rate be chosen to be compatible with the desired integration time and the span of the frequency space swept in the process of the spectroscopic measurement.

Figure 9:
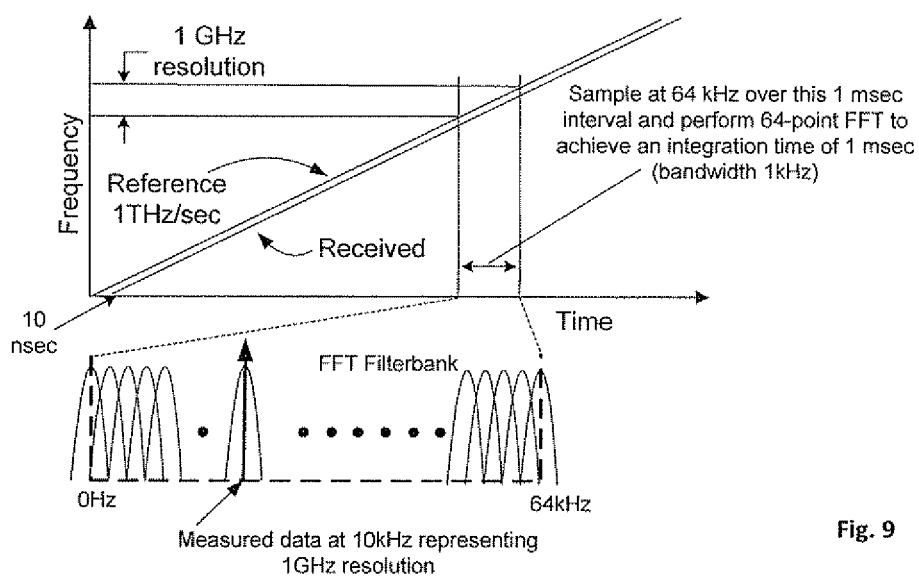
FIG. 9 exemplifies a signal detection process according to some embodiments of the invention for implanting the depth profiling.

For example, if 1 THz span is swept in 1 second and the required integration time is 1 msec, the FFT collection time for each resolvable measurement will be 1 msec and 1000 FFTs will be required to cover the 1 THz span at a resolution of 1 GHz. In this example, if the time delay is designed to be 10 nsec, the frequency at which data is found in the FFT is 10 kHz. The FFT sampling frequency may be chosen to support the expected frequency of the data and the FFT size adjusted accordingly. The interpolation algorithm takes care of the fact that there will not be a harmonic relationship between the FFT sampling frequency and the frequency at which the measured data appears, so the data will split over a few FFT bins. This process is illustrated in FIG. 9.

It is recognized in this invention that the process maps delay between reference and received signals into a frequency location in the FFT. This means that delay can be measured by observing frequency location. The defining relationship is that τ=f/β, where f is the frequency observed in the FFT (i.e. beat frequency at the receiver). The resolution interval associated with this delay measurement is c/β·T, where c is the speed of light and T is the duration of the coherent processing dwell. This recognition is the key to 3D imaging or depth profiling of the sample, where the two spatial dimensions are obtained by positioning the transmitter and receiver transducers relative to the target object and the third dimension (radial distance) is obtained from the position of the signal response in the FFT filter-bank. The delay measured is a round trip delay which converts to a radial range according to the following: R=c·τ/2. It should be noted that preferably, in order to get a phase reference (position in space of a sample) calibration of the free space path prior to the measurements on the sample might be needed.

Figure 10:
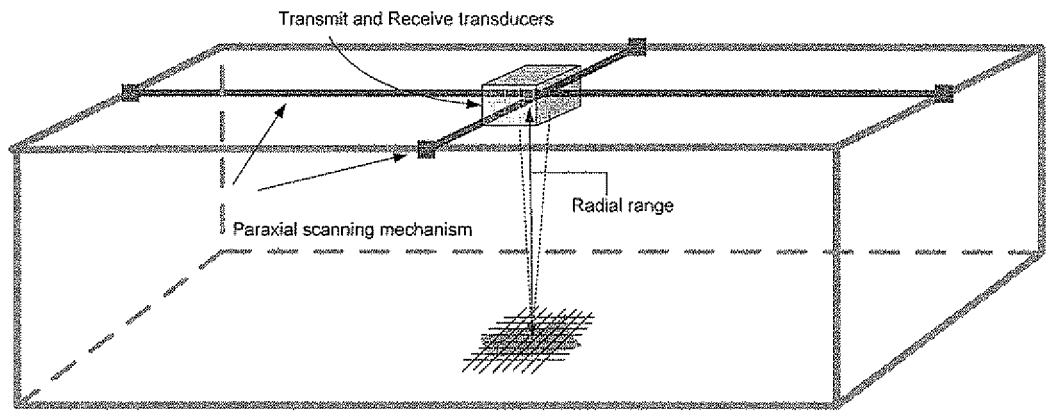
FIG. 10 illustrates schematically an arrangement suitable for depth profiling of the invention.

An arrangement suitable for 3D imaging is illustrated in FIG. 10. According to the invention, parameter, β, which is the linear sweep rate, may be exaggerated, or the processing dwell, T, is chosen to achieve the desired resolution parameter in the radial dimension. For example, if (β·T)=30 GHz, the radial resolution (spatial resolution) will be 1 cm and the spectroscopic resolution is 30 GHz. The property of radial resolution is advantageous in spectroscopic measurement for the purpose of eliminating multi-path reflections. Such reflections exhibit delays different from the delay of the wanted target object and hence are gated in the FFT into filters (bandwidths) that are separated from the filter containing the desired target response.

The parameter β is controlled by temperature variation of the laser(s) or by current modulation of the laser(s). Temperature variation is relatively low speed process, while current modulation may be achieved at electronic speeds. The scale factor pertaining to temperature control on a single laser is approximately 30 GHz/deg. K for lasers near 800 nm wavelength. The scale factor relating frequency variation to laser drive current is approximately 1.6 Ghz per mA.

Figure 11:
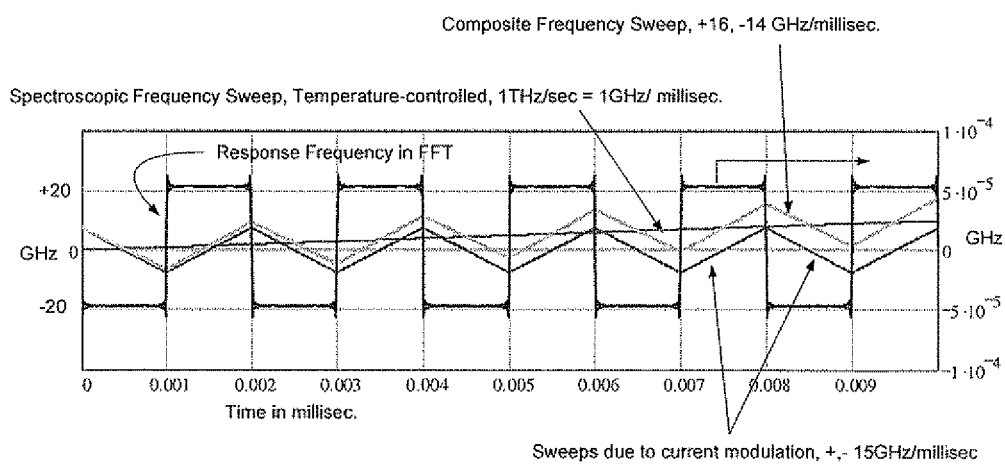
FIG. 11 shows an example of the invention for achieving global and local frequency sweeping rates.

According to the invention, "slow" temperature variation (gradual temperature change) may be used for spectroscopic coverage while fast current modulation may be used simultaneously to achieve radial resolution. In this case, the laser(s) will be driven by a saw-tooth or triangular current waveform while the temperature may be varied simultaneously in a linear fashion. This is illustrated in FIG. 11.

Thus, the present invention provides a simple and effective solution for high-quality spectroscopy in high-frequency applications (e.g. THz applications). The invention provides for high signal-to-noise spectroscopic measurements and also enables depth profiling or 3D imaging of the sample under inspection with high resolution in both spatial and frequency domains.

The invention claimed is:

1. A method for use in spectroscopic measurements of a sample, the method comprising:
    generating inspecting and reference electro-magnetic radiation components of substantially the same frequency contents, said inspecting and reference electro-magnetic radiation components being swept according to a predetermined frequency pattern,
    directing said inspecting and reference radiation components to a detector along first and second different paths, respectively,
    allowing interaction of the inspecting radiation component with a sample located in the first path, thereby inducing a frequency difference between a frequency content of the inspecting radiation component and the reference radiation component interacting at the detector a signal resulting from said interaction between said inspecting and reference radiation components being indicative of one or more properties of the sample at a location where said inspecting radiation interacts with the sample; and
    controlling at least one of said predetermined pattern and the propagation of the inspecting and reference radiation components to the detector;
    wherein said controlling of said predetermined pattern of the frequency sweeping comprises concurrently affecting a firs, global frequency sweeping rate during a certain time period and a local modulation of the frequency sweeping with a second higher sweeping rate.

2. The method of claim 1, wherein said predetermined pattern is selected in order to provide at least one of the following: (i) said frequency difference being highly sensitive to a difference between said first and second paths thereby increasing spatial resolution of detection of a depth location of the interaction between the inspecting radiation component and the sample; and (ii) said frequency difference being within a certain frequency range thereby increasing signal to noise ratio of detection of said one or more properties of the sample.

3. The method of claim 1, wherein at least one of the inspecting and reference radiation components is formed by at least one pair of interacting light beams, said frequency of said at least one of the inspecting and reference radiation components being a beat frequency of said interaction.

4. The method of claim 1, wherein said controlling of the propagation of the inspecting and reference radiation components to the detector comprises allowing free propagation of the reference radiation component to the detector independently of a propagation time of the inspecting radiation to the detector, thereby inducing said predetermined frequency difference and enabling to increase said frequency difference thereby increasing signal to noise of the measurements.

5. The method of claim 1, wherein the inspecting and reference radiation components are formed by first and second pairs of the light beams of the same beat frequency contents which are produced by splitting output light from a light source comprising at least two lasers.

6. The method of claim 1, wherein said controlling of the predetermined pattern of the frequency sweeping comprises gradually changing an operational temperature of an active region of at least one laser generating at least one of the inspecting and reference radiation components thereby causing a substantially monotonic change in the frequency output thereof corresponding to said global frequency sweeping rate, and concurrently modulating an electric current through at least one laser thereby inducing said local frequency modulation in the frequency output of the laser diode corresponding to said higher sweeping rate.

7. The method of claim 1, wherein a first characteristic time scale of said monotonic change in the frequency output is longer than a second characteristic time scale of the frequency modulation, said frequency modulation thereby presenting a sequence of local changes in the frequency output during a global change corresponding to said monotonic change in the frequency output.

8. The method of claim 1, wherein the frequency of the inspecting and reference radiation components being an operative frequency of the inspecting radiation component is in a THz regime.

9. A system for use in spectroscopic measurements of a sample, the system comprising: a radiation transmitter unit configured and operable for generating inspecting and reference electro-magnetic radiation components of substantially the same frequency contents, and for sweeping said frequency according to a predetermined pattern; and a detector located in a first path of the inspecting radiation components after passing through a sample and in a second path of the reference radiation component directly propagating from the transmitter unit, said system being configured to induce a predetermined frequency difference between a frequency of the inspecting radiation component and the reference radiation component interacting at the detector such that a signal resulting from said interaction between the inspecting and reference components being indicative of one or more properties of the sample at a location where said inspecting radiation interacts with the sample; wherein said system is further configured and operable for controlling at least one of said predetermined pattern and the propagation of the inspecting and reference radiation components to the detector, and wherein said controlling of said predetermined pattern of the frequency sweeping comprises concurrently affecting a first, global frequency sweeping rate during a certain time period and a local modulation of the frequency sweeping with a second higher sweeping rate.

10. The system of claim 9, wherein said predetermined pattern is selected in order to provide at least one of the following: (i) said frequency difference being highly sensitive to a difference between said first and second paths thereby increasing spatial resolution of detection of a depth location of the interaction between the inspecting radiation component and the sample; and (ii) said frequency difference being within a certain frequency range thereby increasing signal to noise ratio of detection of said one or more properties of the sample.

11. The system of claim 9, wherein at least one of the inspecting and reference radiation components is formed by at least one pair of interacting light beams; said frequency of said at least one of the inspecting and reference radiation components being a beat frequency of the light beams interaction.

12. The system of claim 9, wherein said reference radiation component propagate to the detector independently of a propagation time of the inspecting radiation component to the detector, thereby inducing said predetermined frequency difference and enabling to increase said frequency difference thereby increasing signal to noise of the measurements.

13. The system of claim 9 comprising:
a light source comprising at least two lasers generating said first and second pairs of the light beams of the same beat frequency contents;
a frequency sweeping module adapted for affecting gradual change of one or more operational parameters of a light source to thereby cause gradual sweeping of the frequency of the light source corresponding to said global frequency sweeping rate across a certain frequency range; and
a frequency modulation module adapted for modulating one or more operational parameters of the light source to induce modulation in the frequency of light source with said second higher sweeping rate.

14. The system of claim 13, wherein said at least two lasers comprise DFB lasers and said gradual change of said one or more operational parameters comprises a gradual change of the operational temperature of an active region of at least one DFB laser affecting substantially monotonic sweeping of the frequency of said at least one DFB laser.

15. The system of claim 14, wherein said frequency sweeping module comprises at least one temperature control unit connectable with at least one TEC system thermally coupled with at least one of the DFB laser; said temperature control unit is configured and operable for controlling the operation of said at least one TEC system.

16. The system of claim 13, wherein said frequency modulation module comprises at least one current control unit connectable to at least one laser diode and configured and operable for modulating an electric current flowing through said at least one laser diode to thereby induce modulation in the frequency of said at least one laser diode.

17. The system of claim 13, adapted for operating said frequency sweeping module and said frequency modulation module concurrently.

18. The system of claim 13, wherein the output from said light source is obtained by coupling light beams from said at least two lasers.

19. The system of claim 13, wherein a first characteristic frequency variation rate in the output frequency of the light source obtained by operating said frequency sweeping module is lower than a second characteristic frequency variation rate obtained by operating said frequency modulation module, said modulation in the frequency of light source thereby presenting a sequence of local changes in the frequency output during a global change corresponding to said gradual sweeping in the frequency output.

* * * * *